United States Patent [19]
Hammarström et al.

[11] Patent Number: 6,142,958
[45] Date of Patent: Nov. 7, 2000

[54] SENSOR AND GUIDE WIRE ASSEMBLY

[75] Inventors: Ola Hammarström, Lerdala; Per Benkowski, Uppsala; Pär von Malmborg, Uppsala; Lars Tenerz, Uppsala, all of Sweden

[73] Assignee: Radi Medical Systems AB, Uppsala, Sweden

[21] Appl. No.: 09/349,980

[22] Filed: Jul. 9, 1999

Related U.S. Application Data

[60] Provisional application No. 60/113,810, Dec. 23, 1998.

[51] Int. Cl.[7] ............................. A61B 5/00; A61M 25/00
[52] U.S. Cl. .......................................... 600/585; 600/486
[58] Field of Search ..................................... 600/433, 434, 600/435, 485, 486, 504, 505, 585, 561

[56] References Cited

U.S. PATENT DOCUMENTS

| | | | |
|---|---|---|---|
| Re. 35,648 | 11/1997 | Tenerz et al. ............................. | 128/673 |
| 4,456,013 | 6/1984 | De Rossi et al. ........................ | 128/675 |
| 4,722,348 | 2/1988 | Ligtenberg et al. ..................... | 128/675 |
| 5,490,323 | 2/1996 | Thacker et al. .......................... | 607/122 |
| 5,517,989 | 5/1996 | Frisbie et al. ............................ | 600/585 |
| 5,715,827 | 2/1998 | Corl et al. ................................. | 128/673 |
| 5,749,371 | 5/1998 | Zadini et al. ............................. | 600/585 |
| 5,779,643 | 7/1998 | Lum et al. ................................ | 600/462 |
| 5,931,819 | 8/1999 | Fariabi ..................................... | 604/525 |
| 5,938,624 | 8/1999 | Akerfeldt et al. ........................ | 600/585 |

FOREIGN PATENT DOCUMENTS

| | | |
|---|---|---|
| 0 728 495 | 10/1996 | European Pat. Off. . |
| 0 879 616 | 11/1998 | European Pat. Off. . |
| 90/01294 | 2/1990 | WIPO . |
| WO 97/00641 | 6/1996 | WIPO . |
| WO 97/27802 | 1/1997 | WIPO . |

*Primary Examiner*—Cary O'Connor
*Assistant Examiner*—Charles Marmor, II
*Attorney, Agent, or Firm*—Foley & Lardner

[57] ABSTRACT

A sensor and guide wire assembly includes a core wire having a distal end, a proximal end, and a plurality of sections of different cross sections and thereby different flexibilities. At least one of the core wire sections has an enlarged portion with a sensor receptacle therein. The assembly also includes a tube that encloses the core wire over at least a fraction of its length such that the core wire extends out from a distal end of the tube. The tube is configured to enable the sensor and guide wire assembly to be inserted into an artery and to be passed to a measurement site inside a patient's body. The assembly further includes a sensor mounted in the sensor receptacle of the enlarged portion of the core wire. A first coil is arranged to enclose a first portion of the core wire extending out from the distal end of the tube, and the first coil is located nearer to the proximal end of the core wire than the sensor. A second coil is arranged to enclose a second portion of the core wire extending out from the distal end of the tube. The second coil is located nearer to the distal end of the core wire than the sensor.

20 Claims, 5 Drawing Sheets

SENSOR AND GUIDE WIRE ASSEMBLY

The applicants hereby claim the benefit of provisional application Ser. No. 60/113,810, filed Dec. 23, 1998, the entire contents of which are incorporated herein by reference.

BACKGROUND OF THE INVENTION

The present invention relates to a sensor and guide wire assembly for intravascular pressure measurements having improved handling properties in the vessels in which it is to be inserted.

A sensor mounted on a guide wire suitable for use in intravascular pressure measurements is disclosed in International Patent Application No. WO 90/01294 and in U.S. Pat. No. Re. 35,648, and U.S. Pat. No. 5,715,827. One known sensor and guide wire assembly comprises a core wire having segments of varying thicknesses in at least the distal region of the core wire. In situations where it is desirable to attach a sensor having electrical leads connected thereto to the core wire, the core wire is enclosed in a tube, and the electrical leads run parallel inside the tube along the core wire. The core wire may, but need not, extend all the way to the proximal end of the tube. If the sensor is a pressure sensor, it is preferable to provide some sort of stiffening member for the sensor in order to avoid mechanical artifacts due to, for example, bending. It is known to provide a short, protective tube segment enclosing the sensor to stiffen and protect the sensor region of the guide wire. A stiffening member of this type has several limitations, however.

A first drawback of a protective tube segment, of the type indicated above, is that the formation of a joint between the coils and protective tube segment is difficult to make, and mismatch often occurs between coil and tube. Put another way, it is difficult to obtain good concentric matching.

A second drawback of a protective tube segment relates to the manufacturing process, which becomes more complicated because an additional structure, i.e., the protective tube segment, must be assembled as part of the sensor and guide wire assembly. A conventional means of attaching the protective tube segment to the sensor is with glue or another suitable adhesive, but this attachment method renders the joint non-optimal from a mechanical point of view. Further, the thermal expansion coefficient of the adhesive may differ from that of the materials used in the remaining components of the sensor and guide wire assembly, which can cause problems. The protective tube segment also makes the sensor region relatively stiff, and the length of the protective tube segment cannot be made as short as desirable.

A third drawback of a protective tube segment is that the tube segment constitutes an asymmetric and non-flexible or stiff portion that hinders bending at turns in a vessel.

A fourth drawback of a protective tube segment is that the inner diameter of the tube segment puts limitations on how the segmenting of the wire can be achieved.

The difficulties suggested in the proceeding are not intended to be exhaustive but rather are among many which tend to reduce the effectiveness and manufacturing efficiencies of conventional sensor and guide wire assemblies. Other noteworthy problems may also exist; however, those presented above should be sufficient to demonstrate that such assemblies appearing in the past will admit to worthwhile improvement.

SUMMARY OF THE INVENTION

Thus, there exists a need for a sensor and guide wire assembly having improved bending characteristics in the region of the sensor.

An object of the invention is therefore to provide a sensor and guide wire assembly that exhibits a smoother transition where the sensor element is placed and that is easier to produce from a manufacturing point of view.

A preferred embodiment of the invention, which is intended to accomplish the foregoing objects, includes a sensor and guide wire assembly having a mounting member. The mounting member preferably comprises an enlarged portion having a sensor receptacle or recess in which the sensor is mounted. This assembly yields an overall stiffer and mechanically robust device, without the drawbacks associated with a separate, protective tube segment as outlined in the above discussion of conventional devices. The assembly of the invention does not require a protective tube segment because the enlarged portion, having a sensor receptacle or recess formed therein, provides a protected mounting site for the sensor.

A sensor and guide wire assembly in accordance with the invention may comprise a core wire having a distal end, a proximal end, and a plurality of sections of different cross sections and different flexibilities. At least one of the sections has an enlarged portion, and the enlarged portion has a sensor receptacle therein. A tube encloses the core wire over at least a fraction of its length such that the core wire, including the enlarged portion, extends out from a distal end of the tube. The tube is configured to enable the sensor and guide wire assembly to be inserted into an artery and to be passed to a measurement site inside a patient's body. A sensor is mounted in the sensor receptacle of the enlarged portion of the core wire. A first coil is arranged to enclose a first portion of the core wire extending out from the distal end of the tube. The first coil is located nearer to the proximal end of the core wire than the sensor. A second coil is arranged to enclose a second portion of the core wire extending out from the distal end of the tube. The second coil is located nearer to the distal end of the core wire than the sensor. The first coil and the second coil each preferably have an outer diameter that is essentially the same as an outer diameter of the enlarged portion.

Additional objects and advantages of the invention will be set forth in the description that follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

FIG. 1b is a cross-sectional view taken along line b—b in FIG. 1a;

FIG. 5b is a cross-sectional view taken along line b—b in FIG. 5a;

DETAILED DESCRIPTION OF THE PREFERRED EMBODIMENT

Figure 1:
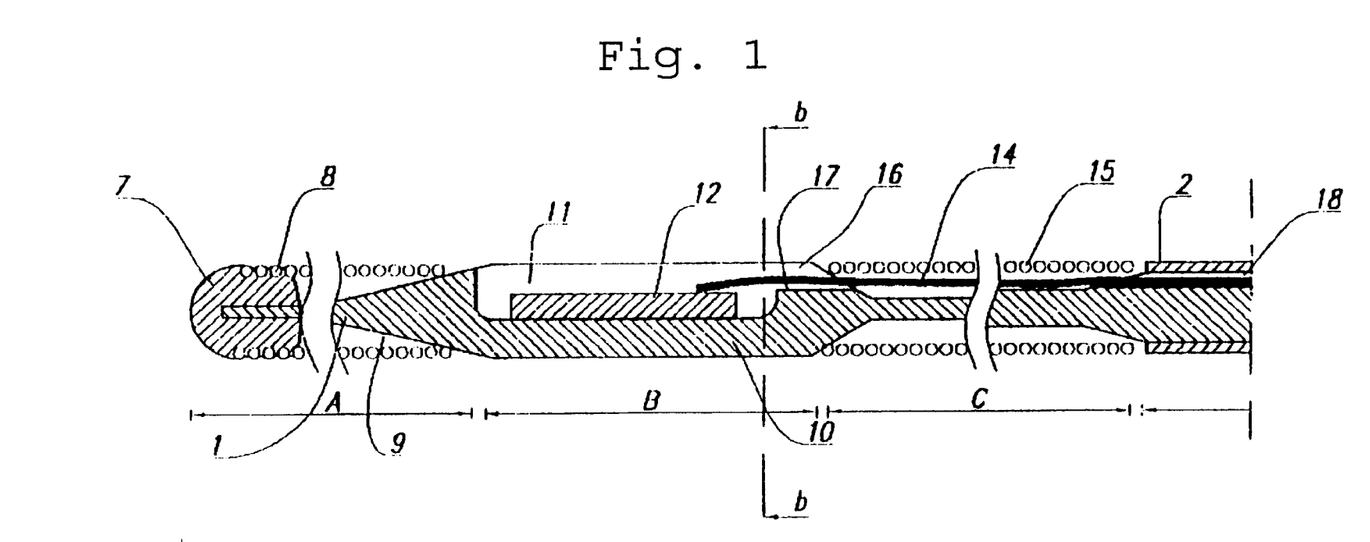
FIGS. 1 and 1a illustrate a longitudinal side view, in cross section, of a full length of a sensor and guide wire assembly according to the invention.
Figure 1A:
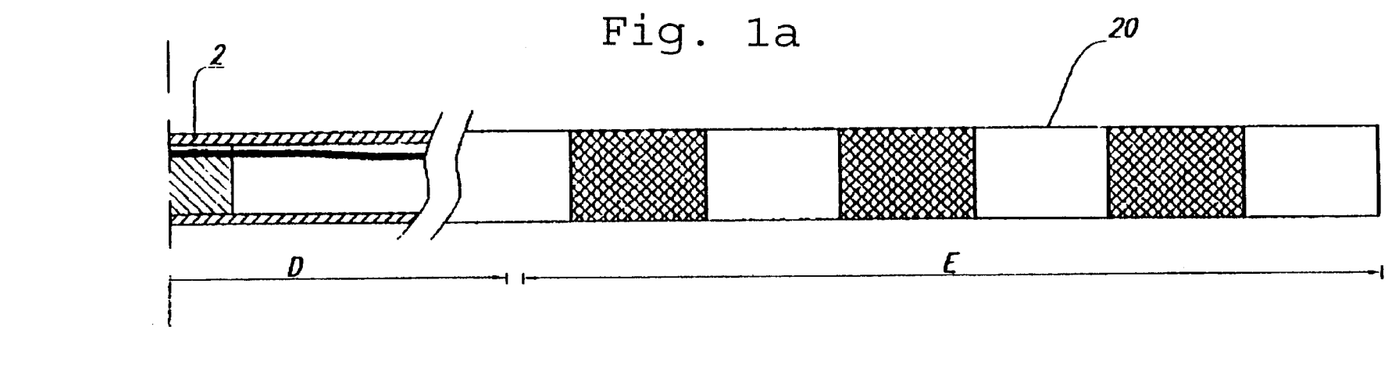

Referring now to the drawings, wherein like numerals indicate like parts, and initially to FIGS. 1 and 1a, there will be seen a preferred embodiment of the sensor and guide wire assembly. As shown in FIGS. 1 and 1a, the assembly generally comprises a core wire 1, a tube 2 in which the core wire 1 at least partially is inserted, at least one coil 8, 15, partially covering a distal portion of the core wire, and a sensor element 12 attached to the core wire 1 in a suitable mounting arrangement (to be described below). The core wire 1 has an enlarged portion 10. The cross section of the enlarged portion 10 has a major dimension that is larger than the major dimension of the cross sections of the remaining portions of the core wire 1. In the case of a cylindrical core wire, the major dimension of the enlarged portion 10 is represented by the diameter of the circular cross section of the core wire, and that diameter is larger than the diameters of the remaining portions of the core wire. In the embodiment of FIGS. 1 and 1a, the distal end of the core wire 10, anchored in tip 7 of the assembly, has a smaller diameter than the diameter of the enlarged portion 10.

For illustrative purposes, the assembly has been divided into five sections, A–E, in FIGS. 1 and 1a. Section A is the most distal portion of the assembly, i.e., that portion which is going to be inserted farthest into the vessel, and section E is the most proximal portion. Section E is provided with a male proximal connector 20. In a preferred embodiment, section A is about 10–50 mm; section B is about 0.5–5 mm; section C is about 200–400 mm; section D is about 500–3500 mm; and section E is about 5–50 mm in length. The diameter of the guide wire varies between 0.25–2 mm. For use in coronary arteries, the diameter is normally 0.35 mm.

Section A preferably includes a radiopaque coil 8, which is made of, for example, platinum or a platinum alloy, usable as a position marker during manipulation of the guide wire. At the very distal end of section A, there is provided a tip 7 having a hemispherical outer shape. The tip 7 may be attached to the coil 8 by welding, soldering, or other suitable attachment methods.

The core wire 1 has an enlarged portion 10 in section B. In the transition area between sections A and B, the proximal end of the coil 8 is attached to the enlarged portion 10 of the core wire 1 with glue, solder, or another suitable adhesive. Alternatively, the coil 8 may be threaded onto the enlarged portion 10 (further details of the coil attachment will be given below). Another coil 15 is attached to a proximal end of the enlarged portion 10. The coil 15 extends over section C for providing flexibility in this region of the core wire 1 and protection of the cables 14.

In the enlarged portion 10, there is provided a sensor receptacle, preferably a slot 11, in which a sensor 12 is mounted. The sensor may, for example, be a pressure sensor. The enlarged portion 10 of the core wire 1, in which the sensor 12 is mounted, decreases the stress exerted on the sensor 12 during sharp vessel turns. Moreover, the enlarged portion 10, by virtue of the provision of the slot 11, protects the sensor 12 from being mechanically destroyed during handling of the core wire 1 or by contact with the vessel wall. The side walls inside the slot 11 should extend a certain distance above the upper surface of the sensor 12 in order to provide the protection desired.

The enlarged portion 10 is preferably made by removing material from a metal wire having the nominal diameter of the enlarged portion so as to form smaller diameter segments extending distally and proximally of the enlarged portion. The machining of the wire can be made by various methods, centerless grinding being a preferred method, although other methods are possible.

Alternatively, the enlarged portion may be made by attaching a short tube segment on a core wire, for example, by soldering. A depression forming a mounting receptacle for the sensor may be made by spark machining. In this way, the overall structure will closely resemble the embodiment of FIGS. 1 and 1a.

Figure 1B:
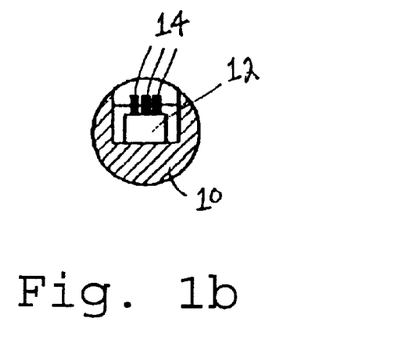

Attached to the sensor 12 are signal transmitting cables 14, the number of which may vary, depending on the design of the sensor. In the embodiment shown, there are three cables (see FIG. 1b). These cables 14 are, for example, attached to the sensor 12 on bond pads (not shown) by bonding or by another suitable technique. The points of attachment of the cables 14 to the sensor 12 are preferably protected from the environment, i.e., from blood or other body fluids. Normally, this may be achieved by filling the slot 11 with silicon rubber or other polymer material to provide adequate protection from such fluids and other environmental impact.

The slot 11 preferably has a width and depth dimension of approximately 50–250 μm and a length dimension of approximately is 50–2500 μm.

As can be seen in FIG. 1a, the slot 11 extends in the proximal direction of the core wire 1 to transform into a shallower recess 16 in which the cables 14 rest. The slot 11 and recess 16 are configured so that the coil 15 does not interfere with or damage the delicate cables 14 when the coil 15 is attached. The relatively shallow recess 16 is defined by a shelf 17 machined in the core wire 1. The main reason for this shelf 17 is that, if the slot 11 were to extend further in the proximal direction of the core wire 1 than the distal edge of the relatively shallow recess 16, the strength of the enlarged portion 10 of the core wire 1 would be inadequate at the transition between sections B and C.

A recess 18, similar to recess 16, is formed in the core wire 1 at the transition between sections C and D, where the core wire 1 is inserted in the tube 2. This recess 18 is provided for the protection of the cables 14, so that they will not be damaged, for example, during assembly.

In the shown embodiment, the core wire 1 extends into the tube 2 only over a relatively short distance in section D. It may be glued in place in the tube 2, although other methods of attachment are possible. However, it is also conceivable, and indeed may be preferable, to let the core wire 1 extend over the entire length of the assembly, all the way up to the proximal connector 20. In this case, it may be necessary to join two pieces to form the core wire, since it may be unfavorable to form a long core wire with enlarged portions via the grinding method. Simply too much metal working would be necessary.

The distal end 9 of the enlarged portion 10, located in section A, preferably is tapered to form a slightly conical extension and functions as an attachment surface for the coil 8. This extension is narrowed down to form a thin wire, which is anchored in the tip 7 of the assembly. The successive tapering of the core wire 1 in section A towards the tip results in a front portion of the guide wire assembly that becomes progressively more flexible nearing the tip 7. This tapering may be obtained by grinding of the metal core wire. It should be noted that the attachment surface of the core wire need not be conical, but rather may be formed as a flattened portion to which the coil and tip may attach.

The coils 8, 15 may be attached to the various parts of the assembly by different methods as will be described.

Figure 2:
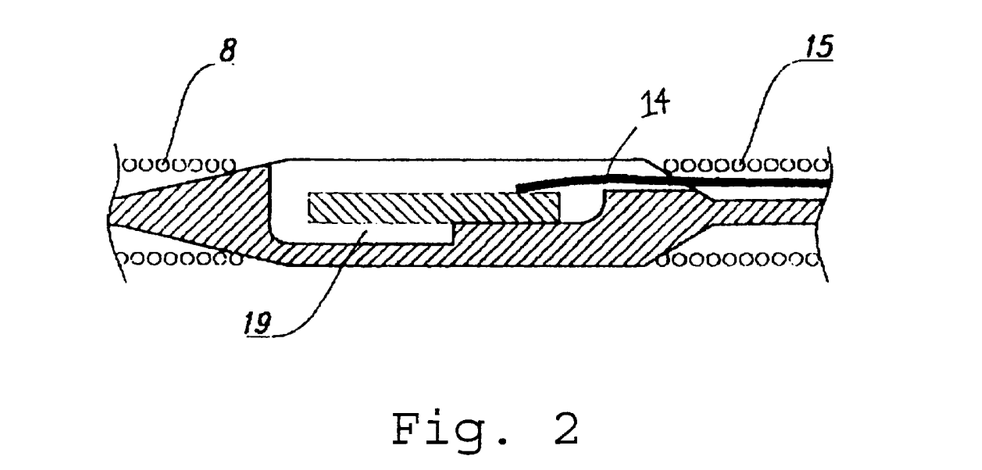
FIG. 2 is a detail side view, in cross section, showing an alternative way of mounting the sensor.

In FIG. 2, an embodiment of the invention is shown wherein a further depression or recess 19 has been formed in the bottom of the enlarged portion 10. The purpose of this recess 19 is to ensure that the distal, pressure sensitive part of the sensor will not experience any mechanical stress, which otherwise could be induced by stress in the enlarged portion 10 if the core wire 1 were bent in the region of sections A-B-C, especially at the transitions between these sections.

As can be clearly seen in FIGS. 1 and 2, the enlarged portion 10 has an outer diameter that is essentially equal to the outer diameter of the coils 8, 15. This will render the diameter of the entire sensor and guide wire assembly the same over the length thereof. The coils and the enlarged portion also will be centered on the longitudinal axis. Furthermore, the outer surface will exhibit no "edges" at the joints between the coils and the enlarged portion that potentially could cause problems during insertion by becoming stuck or hooked in irregularities.

As indicated above, there are several alternative methods of attaching the coils 8, 15 to the enlarged portion 10 and to the tube 2, respectively. Also, there are various alternatives for attachment of the core wire 1 to the tube 2. Some of these alternatives will now be described.

Figure 3:
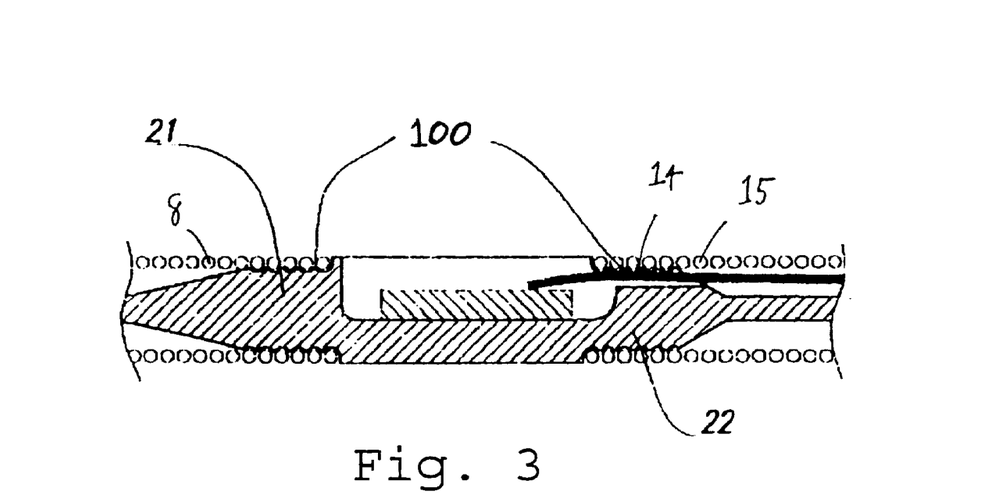
FIG. 3 is a detail side view, in cross section, showing a way of threadedly attaching the coils onto an enlarged portion of a core wire of the sensor and guide wire assembly.

In FIG. 3, an embodiment is shown wherein the coils 8, 15 are threaded (at 100) onto the enlarged portion 10. To this end, the enlarged portion 10 has been made to have distal and proximal extensions 21, 22, respectively, each having a reduced diameter relative to the major part of the enlarged portion 10. The threads 100 are most conveniently made by EDM or micromachining. The number of threads is not critical, but 4–10 threads would be suitable.

Figure 4A:
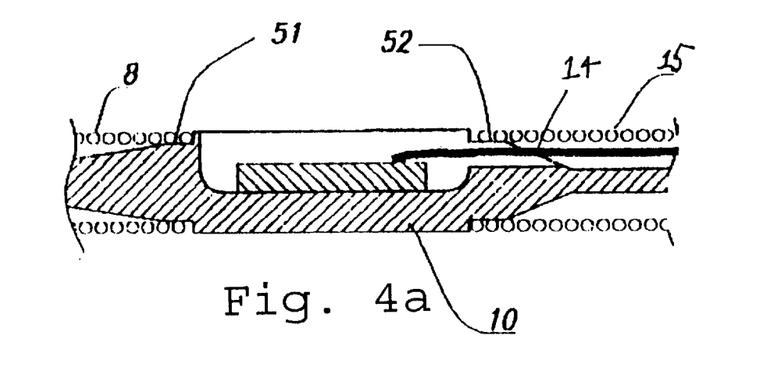
FIG. 4a is a detail side view, in cross section, showing another way of attaching the coils to the core wire.

In FIG. 4a, there are provided distal and proximal extensions 51, 52, respectively, each having a reduced diameter relative to the major part of the enlarged portion 10. The coils 8, 15 are attached thereto, for example, by welding, soldering, or gluing. However, these extensions 51, 52 may be shorter than the extensions 21, 22 of the embodiment in FIG. 3. In both the embodiment of FIG. 3 and of FIG. 4a, it is important that the outer diameter of the coil sections are substantially the same as that of the enlarged portion 10.

Figure 4B:
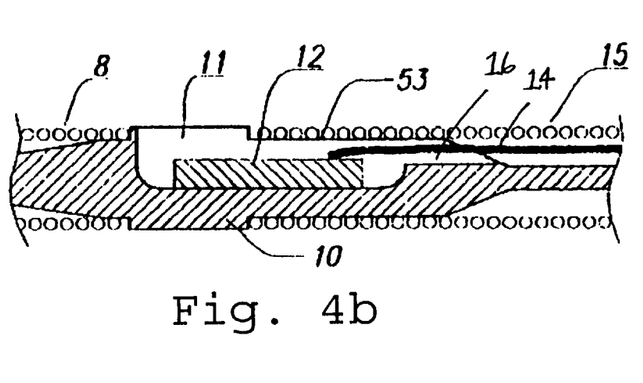
FIG. 4b is a detail side view, in cross section, showing a variation of the embodiment of FIG. 4a, where one coil functions to protect the sensor.

In FIG. 4b, the enlarged portion 10 has been made with a smaller diameter over a larger fraction of its length, to form a proximal extension 53, such that the proximal coil 15, when attached thereto, covers a large fraction (as much as up to ⅔ or more) of the slot 11. Thereby, further protection for the sensor 12 is provided.

Also in these embodiments, the slot 11 extends in the proximal direction so as to form a recess 16, in which the cables 14 may rest for protective purposes.

Figure 5A:
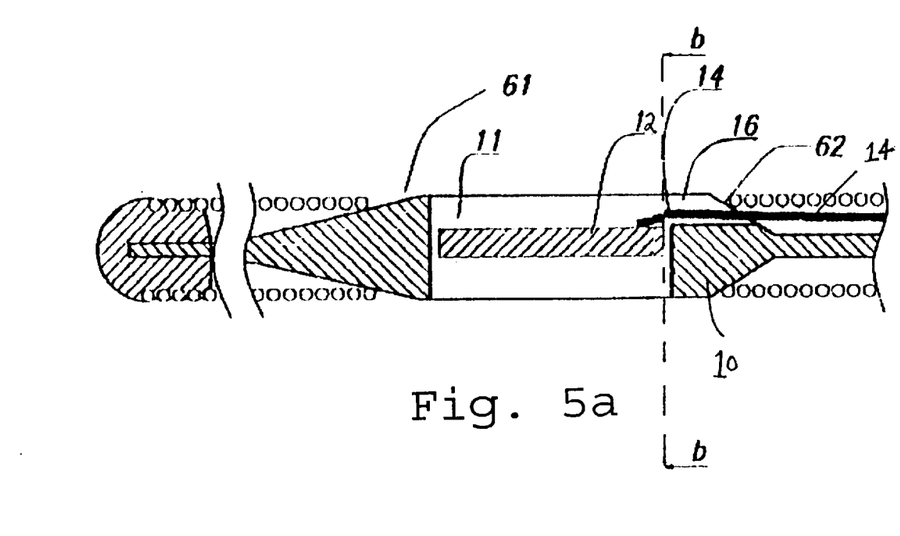
FIG. 5a is a detail side view, in cross section, of an embodiment where a mounting slot for a sensor extends through the enlarged portion.
Figure 5B:
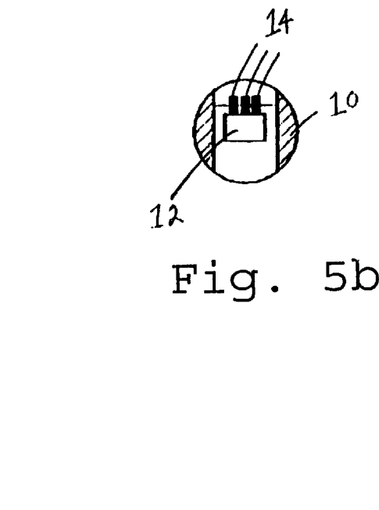

In FIGS. 5a and 5b, an embodiment is shown wherein the slot 11 extends all the way through the enlarged portion 10. In order to fix the sensor 12 in position inside the slot 11, the slot 11 is filled with a material such as silicon rubber or other material. The silicon has a protective effect. Also, in this embodiment, there is provided a recess 16 for accommodating the cables 14.

A particular feature of the enlarged portion 10 of FIGS. 5a and 5b is its tapered extensions 61 and 62, respectively, in distal and proximal directions. As indicated in the introduction, the provision of a protective tube for the sensor tends to cause manufacturing problems because mismatches between the coil and the tube may occur. The quality of the joints also varies considerably, yielding variations in the flexibility in the sensor region from one assembly to another. By forming the enlarged portion 10 with tapered surfaces 61, 62, it becomes relatively easy to mount the coils 8, 15, since the coils 8, 15 may be guided onto the enlarged portion 10 to their mounting positions.

Figure 6:
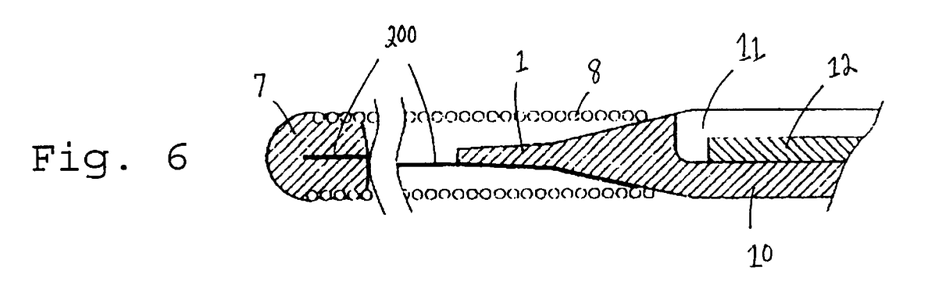
FIG. 6 is a detail side view, in cross section, showing the tip, or distal end, of the sensor and guide wire assembly.

In FIG. 6, it is shown how the core wire 1 can be secured in the tip 7 by attaching a separate wire 200 to the core wire 1 and anchoring it in the tip 7.

Now a number of possibilities of attaching the core wire 1 and coil 15 to the tube 2 will be described with reference to FIGS. 7–13. In all these figures, the core wire 1 is shown to extend only a short distance into the tube 2. However, it may be desirable, from a point of view of providing enough bending strength, to let the core wire 1 extend even all the way through the tube 2 to its proximal end, where a connector (20 as shown in FIG. 1) is provided.

Figure 7:
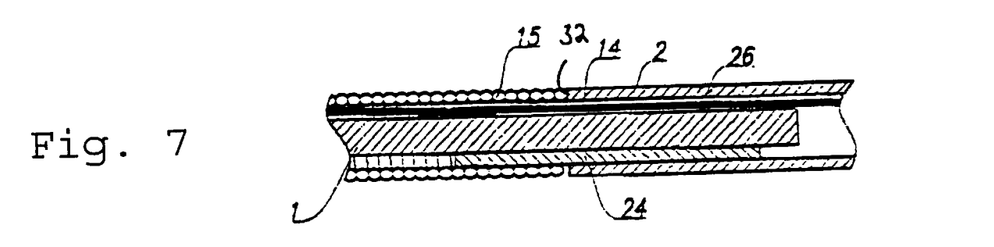
FIG. 7 is a detail side view, in cross section, illustrating one way of attaching a coil to the core wire and to the tube of the sensor and guide wire assembly.

FIG. 7 illustrates an embodiment wherein the core wire 1 has been enclosed in, or inserted in, a tube segment 24 that has an outer diameter corresponding to or being slightly smaller than the inner diameter of the tube 2, in order to obtain a tight fit between the core wire 1 and the tube 2. A longitudinal recess 26 is made in the tube segment 24 for the accommodation of the cables 14. The cross section of the tube segment 24 may resemble a C-shape, where the cables 14 run in the opening of the "C." The material of the tube segment 24 is preferably, but not limited to, polyimide. The material thickness of the tube 2 is preferably substantially the same as the diameter of the wire making up the coil 15. Thereby, the outer diameter of the coil 15 will be essentially equal to the outer diameter of the tube 2. The part of the tube segment 24 that extends out from an edge 32 of the tube 2 functions as a mount for the coil 15. The coil 15 is pushed onto the tube segment 24 and secured thereto by gluing, welding, soldering, or any other suitable technique.

Figure 8:
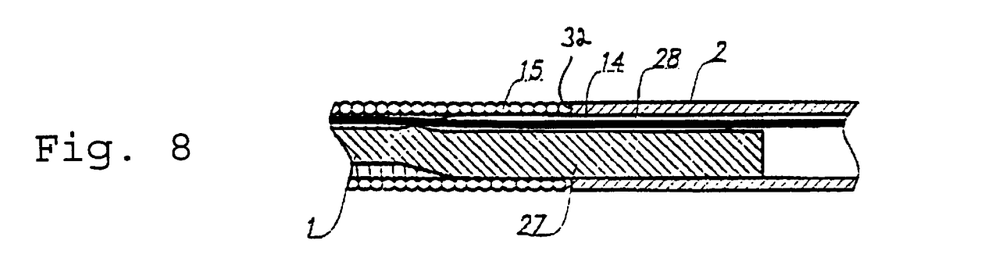
FIG. 8 is a detail side view, in cross section, illustrating an alternative way of attaching a coil to the core wire and to the tube.

In FIG. 8, a tight fit between core wire 1 and tube 2 is obtained by increasing the diameter of the core wire 1 to form a core wire segment 27, the diameter of which corresponds to or is slightly smaller than the inner diameter of the tube 2. For accommodation of the cables 14, a recess 28 is made in the core wire segment 27 by grinding or other machining methods, or some other suitable method. The core wire segment 27 extends out from an edge 32 of the tube 2 to provide a mounting site for the coil 15, similar to the embodiment of FIG. 7.

Figure 9:
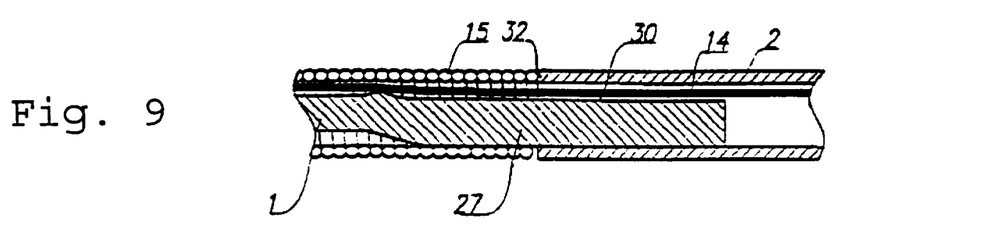
FIG. 9 is a detail side view, in cross section, illustrating a further way of attaching a coil to the core wire and to the tube.

FIG. 9 shows an embodiment, similar to the embodiment of FIG. 8, the difference being that, instead of providing a recess, core wire material has been removed to obtain a planar surface defining a shelf 30. The shelf 30 provides a space for accommodating said cables 14. Whereas the windings of the coil 15 are not visible along the length of the recess 28 from the coil's point of attachment to the tube 2 to a distal end of the recess 28, indicating that the material of the enlarged portion 27 blocks the coil windings from view, the coil windings are visible in the same region in FIG. 9, which illustrates a planar shelf 30 instead of a recess 28. The coil 15 is attached to the core wire segment 27, as in FIG. 8.

Figure 10:
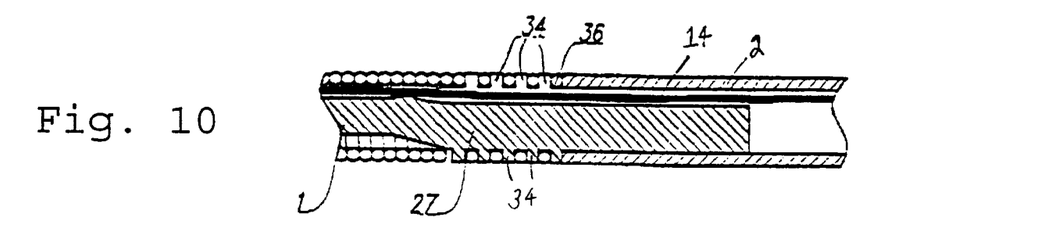
FIG. 10 is a detail side view, in cross section, illustrating a still further way of attaching a coil to the core wire and to the tube.

FIG. 10 illustrates an alternative attachment of the coil 15 to what is disclosed in FIG. 8. Here, the core wire segment 27 has been provided with threads 34 in which the coil windings 36 may be accommodated. Threading in this way may of course be supplemented with gluing or soldering or the like.

Figure 11:
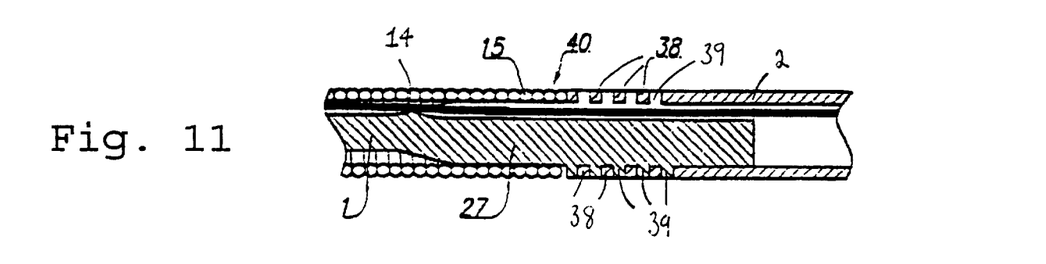
FIG. 11 is a detail side view, in cross section, illustrating another way of attaching a coil to the core wire and to the tube.

FIG. 11 illustrates an embodiment wherein the tube 2 has been machined at its distal end such that a spiral like structure 38 is obtained. The core wire segment 27 of the core wire 1 is provided with threads 39, adapted to cooperate with the spiral like structure 38, to form an engagement between the tube 2 and core wire 1. The coil 15 is attached to the non-threaded part of the core wire segment 27, the non-threaded portion forming a mounting site 40 for the coil 15.

Figure 12:
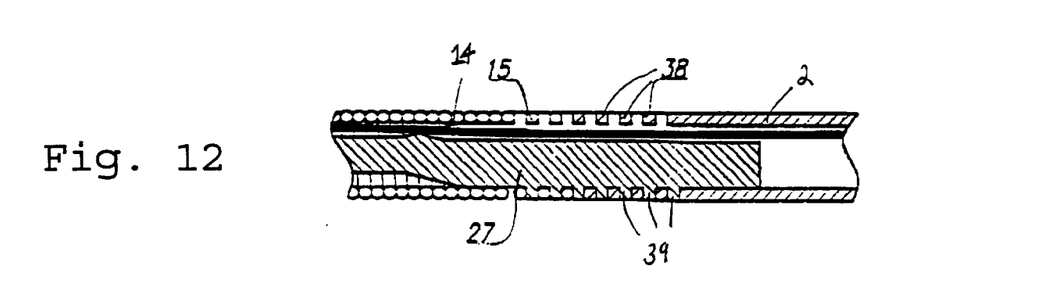
FIG. 12 is a detail side view, in cross section, illustrating a further alternative way of attaching a coil to the core wire and to the tube.

FIG. 12 is a further development of the embodiment of FIG. 11, wherein both the coil 15 and the tube 2 are threaded onto threads 39 of the core wire segment 27. Of course, the attachment of the coil 15 and the threads 39 of the core wire segment 27 to the tube 2 can be supplemented with glue or solder.

Figure 13:
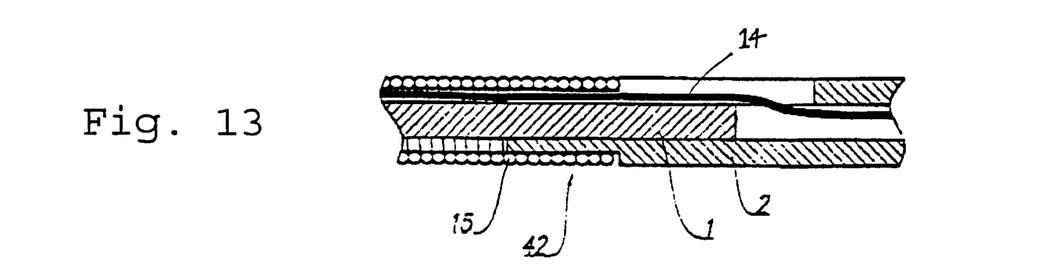
FIG. 13 is a detail side view, in cross section, illustrating still another way of attaching a coil to the core wire and to the tube.

In the embodiment of FIG. 13, the distal end of the tube 2 has a smaller outer diameter and less thickness than a remaining portion of the tube 2 so that the distal end may provide a mounting site 42 for the coil 15.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims.

We claim:

1. A sensor and guide wire assembly comprising:
   a core wire having a distal end, a proximal end, and a plurality of sections of different cross sections and thereby different flexibilities, at least one of said sections having an enlarged portion, said enlarged portion having a sensor receptacle therein;
   a tube enclosing said core wire over at least a fraction of a length of said core wire such that said core wire extends out from a distal end of said tube, said tube being configured to enable said sensor and guide wire assembly to be inserted into an artery and to be passed to a measurement site inside a body;
   a sensor mounted in said sensor receptacle of said enlarged portion of said core wire;
   a first coil arranged to enclose a first portion of said core wire extending out from said distal end of said tube, said first coil being located nearer to said proximal end of said core wire than said sensor; and
   a second coil arranged to enclose a second portion of said core wire extending out from said distal end of said tube, said second coil being located nearer to said distal end of said core wire than said sensor, each of said first coil and said second coil having an outer diameter that is essentially the same as an outer diameter of said enlarged portion.

2. The sensor and guide wire assembly as recited in claim 1, wherein at least one of said first coil and said second coil is a radiopaque coil.

3. The sensor and guide wire assembly as recited in claim 2, wherein at least one of said first coil and said second coil is made of a platinum alloy.

4. The sensor and guide wire assembly as recited in claim 1, further comprising a signal transmitting cable electrically communicating with said sensor to transmit signals from said sensor to a signal processing unit.

5. The sensor and guide wire assembly as recited in claim 4, wherein said sensor is an optical sensor and said signal transmitting cable is an optical cable.

6. The sensor and guide wire assembly as recited in claim 1, wherein said sensor is an electrical sensor and said signal transmitting cable is an electrical cable.

7. The sensor and guide wire assembly as recited in claim 1, wherein said distal end of said core wire is composed of super-elastic alloy.

8. The sensor and guide wire assembly as recited in claim 1, wherein said sensor is selected from the group consisting of a pressure sensor, a temperature sensor, and a combined pressure and temperature sensor.

9. The sensor and guide wire assembly as recited in claim 1, wherein said sensor receptacle comprises a slot in said enlarged portion of said core wire.

10. The sensor and guide wire assembly as recited in claim 9, wherein a depression is formed in said slot to accommodate a pressure sensitive part of said sensor.

11. The sensor and guide wire assembly as recited in claim 1, wherein said enlarged portion of said core wire is provided with threads, and at least one of said first coil and said second coil threadedly engages said threads of said core wire.

12. The sensor and guide wire assembly as recited in claim 1, wherein ends of said enlarged portion are tapered, and at least one of said first coil and said second coil is attached to a respective one of said tapered ends by at least one of soldering, gluing, and welding.

13. The sensor and guide wire assembly as recited in claim 1, wherein said enlarged portion of said core wire includes extensions at a distal end and a proximal end thereof, and at least one of said first coil and said second coil is attached to said extensions at the appropriate end of said enlarged portion by at least one of soldering, gluing, and welding.

14. The sensor and guide wire assembly as recited in claim 1, wherein at least a portion of said sensor is embedded in soft material.

15. The sensor and guide wire assembly as recited in claim 14, wherein said soft material is selected from the group consisting of silicon rubber, latex, and other polymer materials.

16. The sensor and guide wire assembly as recited in claim 1, wherein said sensor receptacle in which said sensor is mounted extends through said enlarged portion, and wherein said sensor is secured in place by embedding said sensor in a soft material selected from the group consisting of silicon rubber, latex, and other polymer materials.

17. A sensor and guide wire assembly, comprising:
   a core wire having a proximal end, a distal end, and an enlarged portion;
   a sensor mounted in said enlarged portion of said core wire, said enlarged portion being an essentially cylindrical member having a slot formed therein to house said sensor, said slot having a width to depth ratio sufficient to provide adequate protection of said sensor from mechanical interference and damage;
   a first coil arranged to enclose a first portion of said core wire, said first coil being located nearer to said proximal end of said core wire than said sensor; and
   a second coil arranged to enclose a second portion of said core wire, said second coil being located nearer to said distal end of said core wire than said sensor.

18. The sensor and guide wire assembly as recited in claim 17, wherein said sensor is secured in place by embedding said sensor in a soft material selected from the group consisting of silicon rubber, latex, and other polymer materials.

19. The sensor and guide wire assembly as recited in claim 17, wherein said slot in which said sensor is mounted extends through said enlarged portion.

20. The sensor and guide wire assembly as recited in claim 17, wherein each of said first coil and said second coil have an outer diameter that is essentially the same as an outer diameter of said enlarged portion.

* * * * *